(12) United States Patent
Bouman et al.

(10) Patent No.: US 7,308,071 B2
(45) Date of Patent: Dec. 11, 2007

(54) METHODS, APPARATUS, AND SOFTWARE FOR RECONSTRUCTING AN IMAGE

(75) Inventors: Charles Addison Bouman, West Lafayette, IN (US); Ken David Sauer, South Bend, IN (US); Jiang Hsieh, Brookfield, WI (US); Jean-Baptiste Thibault, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 377 days.

(21) Appl. No.: 10/991,176

(22) Filed: Nov. 17, 2004

(65) Prior Publication Data

US 2006/0104409 A1    May 18, 2006

(51) Int. Cl.
*A61B 6/03*    (2006.01)

(52) U.S. Cl. .......................... 378/4; 378/901; 382/131

(58) Field of Classification Search ................ 378/4, 378/15, 901; 382/131
See application file for complete search history.

(56) References Cited

U.S. PATENT DOCUMENTS

| | | | |
|---|---|---|---|
| 6,507,633 B1 * | 1/2003 | Elbakri et al. ................. | 378/8 |
| 6,529,575 B1 * | 3/2003 | Hsieh ............................ | 378/4 |
| 2003/0156684 A1 * | 8/2003 | Fessler ....................... | 378/210 |

OTHER PUBLICATIONS

Kamasak et al., Direct Reconstruction of Kinetic Parameter Images from Dynamic PET Data, Conference record of the Thirty-Seventh Asilomar Conference on Signals, Systems & Computers, vol. 2, pp. 1919-1923, Published Nov. 9-12, 2003.*

Thibault et al., Approximate Poisson likelihoods for simple optimization in MAP tomographic estimation, SPIE vol. 3816, pp. 161-171, Jul. 1999.*

Ye et al., Nonlinear multigrid optimization for Bayesian diffusion tomography, Proceedings of the International Conference on Image Processing 1999, vol. 2, pp. 653-657.*

Frese et al., Discrete Multiscale Bayesian Image Reconstruction, Conference record of the Thirty-Second Asilomar Conference on Signals, Systems & Computers, vol. 2, pp. 1687-1691, Nov. 1-4, 1998.*

Bouman et al., A Multiscale Random Field Model for Bayesian Image Segmentation, IEEE Transactions on Image Processing, vol. 3, Issue 2, pp. 162-177, Mar. 1994.*

Lu et al., Adaptive Noise Reduction toward Low-dose Computed Tomography, SPIE, vol. 5030, pp. 759-766, Jun. 2003.*

Comtat et al., Clinical feasible reconstruction of 3D whole-body PET/CT data using blurred anatomical labels, Phys. Med. Biol., vol. 46, pp. 1-20, 2001.*

Charbonnier et al., An adaptive reconstruction method involving discontinuities, IEEE International Conference on Acoustics, Speech, and Signal Processing, 1993, ICASSP-93, vol. 5, pp. 491-494.*

* cited by examiner

*Primary Examiner*—Edward J. Glick
*Assistant Examiner*—John M Corbett
(74) *Attorney, Agent, or Firm*—Armstrong Teasdale LLP

(57) ABSTRACT

A method of reconstructing an image includes substantially minimizing a cost function of the form $$\hat{x} = \operatorname*{argmin}_{x} \left\{ \sum_{m=0}^{M} D_m(y_m, F_m(x)) + S(x) \right\},$$

where $\hat{x}$ is the value of x which achieves the minimum summation, $y_m$ is an integral projection, $F_m(x)$ is an forward projection function, and $S(x)$ is a stabilizing function, to obtain $\hat{x}$, and using the obtained $\hat{x}$ to perform a multislice Computed Tomography (CT) reconstruction to generate an image.

32 Claims, 1 Drawing Sheet

METHODS, APPARATUS, AND SOFTWARE FOR RECONSTRUCTING AN IMAGE

BACKGROUND OF THE INVENTION

This invention relates generally to methods, apparatus and software for image reconstruction.

Traditionally, images have been reconstructed from computed tomography (CT) data using so-called direct reconstruction algorithms such as filtered back projection (FBP) or convolution back projection (CBP). Recently, iterative reconstruction (IR) algorithms have been introduced for the reconstruction of CT images. One advantage of IR algorithms is that they can more accurately model the measurements obtained from real CT systems. This is particularly true for helical CT systems with multi-slice detectors because these systems produce projection measurements that pass obliquely through the 2-D reconstructed image planes. By more accurately modeling these projections, IR algorithms can produce reconstructions with higher quality, lower noise, and fewer artifacts.

For example, consider a helical scan CT system. The 3-D volume to be reconstructed can be represent by an array of N discrete voxels $x_i$ where i is the index of the voxel 3-D position. The value $x_i$ may specify the unknown density of the voxel. Furthermore, let $x=[x_1,x_2, \ldots ,x_N]$ be a vector containing the unknown density of each voxel in the reconstruction. So in this case, x represents the full 3-D reconstruction volume. During the CT scanning process, projections are measured for M different projections through the object. The different projections are typically measured for a wide variety of positions and angles through the object. The value of the integral jth projection through the object is denoted by $y_m$ and the vector of all measurements is denoted by $y=[y_1,y_2, \ldots y_M]$.

The measurement $y_m$ of the CT scanning process can be modeled as being a noisy version of the forward projection of the 3-D volume x. So the $m^{th}$ projection can be analytically computed as $F_m(x)$ where $F_m(\bullet)$ is the forward projection function. The difference between $y_m$ and $F_m(x)$ is caused by noise and distortions when x is chosen to exactly match the true voxel densities of the object being imaged.

The mismatch between the true projection measurement $y_m$ and the analytical forward projection $F_m(x)$ can be evaluated using a distance function of the form $D_m(y_m,F_m(x))$ where the distance function $D_m(\bullet,\bullet)$ penalizes mismatch between $y_m$ and $F_m(x)$. The distance function $D_m(\bullet,\bullet)$ should be large when $y_m$ and $F_m(x)$ are very different and small when $y_m$ and $F_m(x)$ are very similar. The distance function is not required to obey any specific metric properties such as the triangle inequality. In some cases, it can be chosen to have the form $D_m(y_m,F_m(x))=w_m|y_m-F_m(x)|^2$ where $w_m$ is a scalar weight. In some cases, it may be chosen to have the form $D_m(y_m,F_m(x))=p(y_m|F_m(x))$ where $p(\bullet|\bullet)$ is a conditional probability function for a Poisson, Gaussian, or other distribution.

The objective of IR algorithms is to determine the unknown value of x by searching for the value of the vector x that best matches the measured data. Typically, this is done by minimizing a cost function of the form $$\hat{x} = \operatorname*{argmin}_x \left\{ \sum_{m=0}^{M} D_m(y_m, F_m(x)) \right\} \quad (1)$$

where $\hat{x}$ is the value of the variable x which achieves the minimum of the function. This cost function can be minimized in a variety of manners using optimization methods such as iterative coordinate descent, expectation maximization, conjugate gradient, or any number of alternative techniques. In practice, the solution to (1) is often too noisy for clinical use.

BRIEF DESCRIPTION OF THE INVENTION

In one aspect, a method of reconstructing an image is provided. The method includes substantially minimizing a cost function of the form $$\hat{x} = \operatorname*{argmin}_x \left\{ \sum_{m=0}^{M} D_m(y_m, F_m(x)) + S(x) \right\},$$

where $\hat{x}$ is the value of x which achieves the minimum summation, $y_m$ is an integral projection, $F_m(x)$ is a forward projection function, and $S(x)$ is a stabilizing function, to obtain $\hat{x}$, and using the obtained $\hat{x}$ to perform a multislice Computed Tomography (CT) reconstruction to generate an image.

In another aspect, an imaging system includes a radiation source, a detector array including a plurality of cells positioned to receive radiation from the source, and a computer coupled to the detector array. The computer is configured to utilize a cost function of the form $$\hat{x} = \operatorname*{argmin}_x \left\{ \sum_{m=0}^{M} D_m(y_m, F_m(x)) + S(x) \right\},$$

where $\hat{x}$ is the value of x which achieves the minimum summation, $y_m$ is an integral projection, $F_m(x)$ is a forward projection function, and $S(x)$ is a stabilizing function, to obtain $\hat{x}$, and using the obtained $\hat{x}$ and perform a multislice Computed Tomography (CT) reconstruction to obtain an image using the obtained $\hat{x}$.

In yet another aspect, a computer readable medium encoded with a program is provided. The program is configured to instruct a computer to utilize a cost function including a stabilizing function $S(x)$ to obtain a $\hat{x}$ which achieves a minimum summation, and perform a multislice Computed Tomography (CT) reconstruction using the obtained $\hat{x}$ to generate an image.

DETAILED DESCRIPTION OF THE INVENTION

Figure 1:
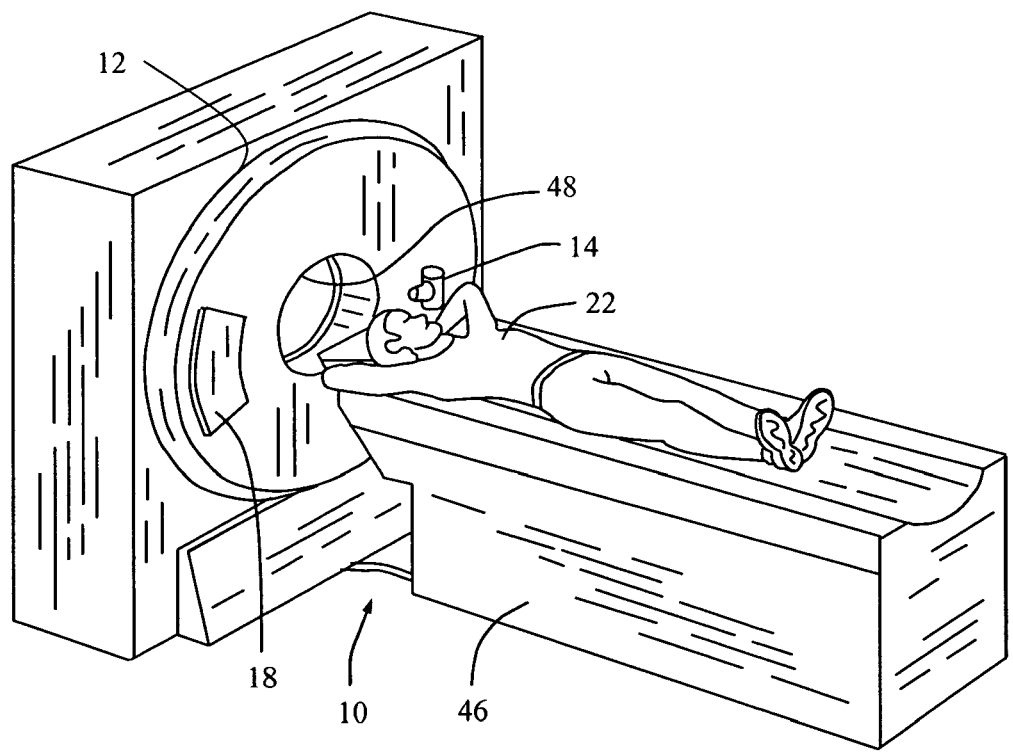
FIG. 1 is a pictorial view of a CT imaging system embodiment.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan maybe performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further improve the data acquisition, multi-slice or volumetric CT is built. Such a system collects multiple projections simultaneously by using a detector consisting of multiple detector rows. In such configuration, the fan beam geometry becomes a cone beam geometry.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
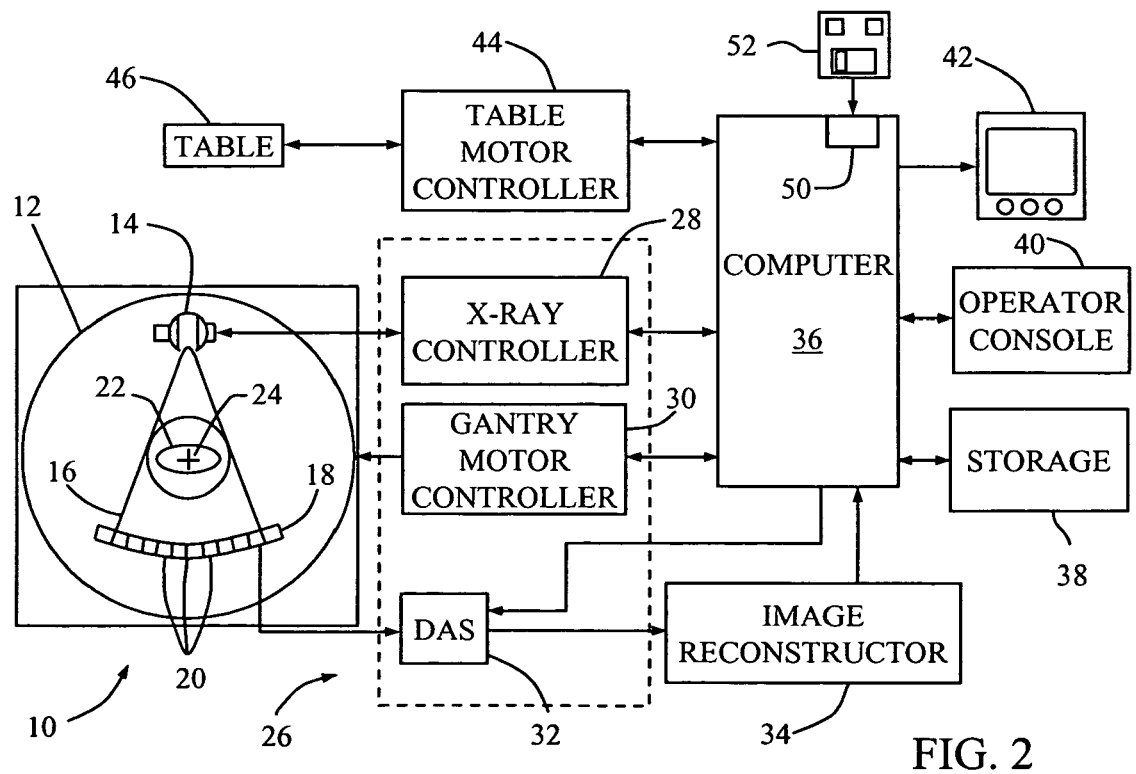
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the embodiments described herein are not limited to practice in CT system 10 and can be utilized in connection with many other types and variations of imaging systems. In one embodiment, computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, field programmable gate arrays (FPGA) and all other programmable circuits.

Herein described are new methods, apparatus, and software for accurate geometric forward modeling of third generation CT scanners that is suitable for iterative reconstruction of high quality clinical images for medical diagnostic purposes. The herein described methods support all configurations of CT scanners, including single-slice and multi-slice CT, as well as any trajectory of acquisition, such as step-and-shoot (axial) mode, helical mode, or any other mode, with constant or varying pitch and sampling patterns. The herein described methods are also applicable to fourth and fifth generation scanners such as an electron beam CT scanner (EBCT) such as are commercially available from GE Imatron of South San Francisco, Calif.

Traditionally, images have been reconstructed from CT data using so-called direct reconstruction algorithms such as filtered back projection (FBP) or convolution back projection (CBP). New iterative reconstruction (IR) algorithms are being introduced for the reconstruction of CT images. One advantage of IR algorithms is that they can more accurately model the measurements obtained from real CT systems. This is particularly true for helical CT systems with multi-slice detectors because these systems produce projection measurements that pass obliquely through the 2-D reconstructed image planes. By more accurately modeling these projections, IR algorithms can produce reconstructions with higher quality, lower noise, and fewer artifacts.

For example, consider a helical scan CT system. The 3-D volume to be reconstructed can be represent by an array of N discrete voxels $x_i$ where i is the index of the voxel's 3-D position. The value $x_i$ may specify the unknown density of the voxel. Furthermore, let $x=[x_1, x_2, \ldots, x_N]$ be a vector containing the unknown density of each voxel in the reconstruction. So in this case, x represents the full 3-D reconstruction volume. During the CT scanning process, projections are measured for M different projections through the object. The different projections are typically measured for a wide variety of positions and angles through the object. The value of the integral jth projection through the object is denoted by $y_m$ and the vector of all measurements is denoted by $y=[y_1, y_2, \ldots, y_M]$.

The objective of IR algorithms is to determine the unknown value of x by searching for the value of the vector x that best matches the measured data. This has been is done by minimizing a cost function of the form $$\hat{x} = \operatorname*{argmin}_x \left\{ \sum_{m=0}^{M} D_m(y_m, F_m(x)) \right\} \qquad (1)$$

where $\hat{x}$ is the value of the variable x which achieves the minimum of the function, and wherein F is a transformation of the image space x. This cost function can be minimized in a variety of manners using optimization methods such as iterative coordinate descent, expectation maximization, conjugate gradient, or any number of alternative techniques.

In practice, the solution to (1) is often too noisy. This noisiness may result when there are two few measurements, when the quality of the measurements is poor, or when the available projection angles and locations do not give sufficient information about x to properly reconstruct it. This problem can be addressed by adding an additional stabilizing functional S(x) to the cost function being minimized. This results in the regularized inverse $$\hat{x} = \operatorname*{argmin}_x \left\{ \sum_{m=0}^{M} D_m(y_m, F_m(x)) + S(x) \right\} \qquad (2)$$

In one embodiment, the function S(x) is chosen to be a quadratic function with the form $S(x)=x^t H x$ where H is a symmetric and positive definite or positive semi-definite matrix. The particular choice of the functional S(x) can have a substantial effect on the quality of reconstructions produced by IR algorithms.

In one embodiment, the IR CT reconstruction works by minimizing a cost function of (2) above where S(x) is a quadratic or nonquadratic functional that penalizes differences in neighboring pixels without excessively penalizing the large differences that occur along discontinuities or edges in the reconstructed images. Such functions are said to be edge preserving.

Reconstruction quality can be improved by choosing S(x) to have the form $$S(x) = \sum_{\{i,j\} \in N} \rho\left(\frac{x_i - x_j}{\sigma b_{i,j}}\right) \qquad (3)$$

where $\rho(.)$ is a substantially convex function, i and j are the indexes of two voxels in a 2, 3, 4 or higher dimensional reconstructed image, $b_{i,j}$ is a scalar weight that depends on the positions of the neighboring pixels $x_i$ and $x_j$, and $\sigma$ is a scaling parameter that controls overall smoothness of the reconstruction. The derivative of $\rho(.)$ can be an increasing function, so that when $\Delta_2 > \Delta_1$ then $$\frac{d\rho(\Delta_2)}{d\Delta_2} \geq \frac{d\rho(\Delta_1)}{d\Delta_1}$$

A particular selection for the function $\rho(.)$ is $$\rho(\Delta) = \Delta^p \qquad (4)$$

where p is a scalar constant typically selected in the range of $2 \geq p \geq 1$. In this case, selecting a larger value of p produces a smoother reconstruction with less edge detail while selecting a smaller value of p produces a reconstruction with better edge detail.

The reconstruction quality can be further improved by adaptively adjusting the values of the constants $b_{i,j}$. More specifically, the values of $b_{i,j}$ can be reduced at or near locations of discontinuities in the reconstructions and can be increased in smooth areas. This method can be used for a wide variety of functions $\rho(.)$, and in particular is useful when p=2. The values of $b_{i,j}$ can adaptively be chosen based on a number of measures of local smoothness in the reconstruction. These local measures include the local variations in the reconstruction being computed, the local variations in a reconstruction produced using a direct reconstruction method such as filtered back projection, or the results of a coarser scale reconstruction.

An adaptive method based on local variations in a direct reconstruction works by spatially adapting the values of $b_{i,j}$ based on the difference in corresponding pixels in the direct reconstruction. So for example, let $z_i$ be the image obtained by direct reconstruction. Then the weights can be computed by $$b_{i,j} = |z_i - z_j| \qquad (5)$$

Alternatively, $b_{i,j}$ can by computed by using (5) but with spatial smoothing applied first to $z_i$ or afterwards to $b_{i,j}$.

An alternative approach is to adapt the values of $b_{i,j}$ based on the differences in the pixels in a lower resolution IR reconstruction. So for example, let $L_{(m,n)}$ be a 2-D slice of the reconstruction at a resolution that has ½ the resolution and let (m,n) be the index of the row and column of the pixel. Furthermore, let $x_{(k,l)}$ be a pixel of the full resolution reconstruction at 2-D location (k,l), and let $b_{(m,n),(k,l)}$ be the corresponding weights for pixel pairs. Then the weights can be computed by $$b_{(2m,2n),(2k,2l)} = |L_{(m,n)} - L_{(k,l)}| \qquad (6)$$

Alternatively, $b_{(m,n),(k,l)}$ can by computed by using (6) but with spatial smoothing applied first to $L_{(m,n)}$ or afterwards to $b_{(m,n),(k,l)}$.

More specifically, the values of $b_{i,j}$ can be increased at or near locations of discontinuities in the reconstructions and can be reduced in smooth areas. This method can be used for a wide variety of functions $\rho(.)$, and in particular is useful when p=2. The values of $b_{i,j}$ can adaptively be chosen based on a number of measures of local smoothness in the reconstruction. These local measures include the local variations in the reconstruction being computed, the local variations in a reconstruction produced using a direct reconstruction method such as filtered back projection, or the results of a coarser scale reconstruction.

Alternatively, the reconstruction quality can be improved by adaptively adjusting the values of the constants $b_{i,j}$ based on the local properties of the material or structure being reconstructed. So for example, the best value of $b_{i,j}$ for dense bone regions in a medical image can be different than the best value of $b_{i,j}$ for a soft tissue region. Typically, the different materials or structures in a reconstruction can be separated by first using the reconstructed image from an alternative reconstruction algorithm such as FBP and then segmenting this image into the distinct materials or structures based on local density, texture, shape, or other properties. Alternatively, the different materials or structures can be separated by segmenting reconstructions from one or more other imaging modalities using intensity, texture, shape, or other properties. These segmentation processes may also use a priori knowledge of the scanned object and its material properties, texture, shape, and other properties.

In some cases, it may be valuable to vary the $\rho(.)$ as a function of position in the reconstruction. In this case, the equation for $S(x)$ has the form $$S(x) = \sum_{\{i,j\} \in N} \rho_{i-j}\left(\frac{x_i - x_j}{\sigma b_{i-j}}\right) \quad (7)$$

where the function $\rho_{i,j}(.)$ can vary depending on the particular voxels, i and j. A particular selection for the function $\rho_{i,j}(.)$ is $$\rho_{i,j}(\Delta) = \Delta^{p_{i,j}} \quad (8)$$

where $\rho_{i,j}$ is a scalar value which may vary with the voxel indexes i and j. All the adaptive methods described above for $b_{i,j}$ can be applied for $\rho_{i,j}$.

In some cases, the reconstruction quality can be improved by adapting the values of the neighborhood N based on the spatial content of the reconstruction. So define $$N_i = \{j: \{i,j\} \in N\} \quad (9)$$

Then $N_i$ is the set of neighboring voxels to the voxel at location i. The set can be adapted to best account for the voxel local properties. The choice of $N_i$ for each voxel i can be determined adaptively from an image reconstructed using an alternative method such as FBP or an alternative modality such as MRI, PET, or others.

All the adaptation algorithms for $b_{i,j}$, $\rho_{i,j}$, and $N_i$ can be varied based on the clinical protocols. This may be done similarly to the manner in which reconstruction kernels are varied in FBP based on the clinical protocol. For example, for high-resolution chest studies the parameters may be varied to optimized spatial resolution, whereas for liver studies the parameters may be varied to optimize for noise reduction.

While the invention has been described in terms of various specific embodiments, those skilled in the art will recognize that the invention can be practiced with modification within the spirit and scope of the claims.

What is claimed is:

1. A method of reconstructing an image, said method comprising:
   substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m, F_m(x))$ is a distance measure between $y_m$ and $F_m S(x)$, is a stabilizing function, to obtain $\hat{x}$; and generating an image by performing a multislice Computed Tomography (CT) reconstruction using the obtained $\hat{x}$, wherein a weight of $S(x)$ is adaptively adjusted at locations of discontinuities within the reconstructed image.

2. A method in accordance with claim 1, wherein $S(x)$ has the form of $$S(x) = \sum_{\{i,j\} \in N} \rho\left(\frac{x_i - x_j}{\sigma b_{i,j}}\right),$$

where $b_{i,j}$ is the weight, $\rho$ is a function, $\sigma$ is a weight, and $x_i$ and $x_j$ are voxels.

3. A method in accordance with claim 2, wherein $\rho$ is a substantially convex function.

4. A method in accordance with claim 3, wherein $\rho$ has a monotonically increasing derivative.

5. A method in accordance with claim 4, wherein $\rho$ is an exponential function such that $\rho(\Delta) = \Delta^p$ where $2 \geq p \geq 1$.

6. A method in accordance with claim 5, wherein $b_{i,j}$ is adaptively adjusted based upon at least one measure of local smoothness.

7. A method in accordance with claim 2, wherein $b_{i,j}$ is adaptively adjusted based upon at least one measure of local smoothness.

8. A method in accordance with claim 2, wherein $b_{i,j}$ is adaptively adjusted based upon differences of pixels in a reconstruction.

9. A method in accordance with claim 8, wherein $b_{i,j}$ is adaptively adjusted based upon differences of pixels in a reconstruction in accordance with $b_{i,j} = |z_i - z_j|$, where $z_i$ and $z_j$ are pixels, and $2 \geq p \geq 1$.

10. A method in accordance with claim 9 further comprising spatially smoothing at least one of:
    $b_{i,j}$ after calculating $b_{i,j}$, and
    $z_i$ prior to calculating $b_{i,j}$.

11. A method in accordance with claim 2, wherein $b_{i,j}$ is determined using at least two different reconstructions at different resolutions.

12. A method in accordance with claim 11 wherein $b_{i,j}$ is determined in accordance with
    $b_{i,j} = b_{(2m,2n),(2k,2l)} = |L_{(m,n)} - L_{(k,l)}|$, where $L_{(m,n)}$ is a pixel in the reconstruction with less resolution, $L_{(k,l)}$ is a pixel in the reconstruction with greater resolution, and $2 \geq p \geq 1$,
wherein m and n are the respective row and the column indices of $L_{(m,n)}$ and k and l are the respective row and the column indices of $L_{(k,l)}$.

13. A method in accordance with claim 12 wherein the reconstruction with less resolution has ½ the resolution of the reconstruction with greater resolution.

14. A method in accordance with claim 12 further comprising spatially smoothing at least one of:
   $b_{i,j}$ after calculating $b_{i,j}$, and
   $L_{(m,n)}$ prior to calculating $b_{i,j}$.

15. A method in accordance with claim 2 further comprising:
   reconstructing an image;
   segmenting the image; and
   adaptively determining $b_{i,j}$ based upon the segmentation.

16. A method in accordance with claim 2 further comprising adaptively determining $b_{i,j}$ based on position in the image.

17. A method in accordance with claim 2 further comprising adaptively determining $b_{i,j}$ based on at least one neighboring pixel.

18. A method in accordance with claim 2 further comprising:
   receiving a clinical protocol; and
   adaptively determining $b_{i,j}$ based on the received protocol.

19. An imaging system comprising:
   a radiation source;
   a detector array comprising a plurality of cells positioned to receive radiation from said source; and
   a computer coupled to said detector array; said computer configured to:
   utilize a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is an forward projection function, $D_m(y_m, F_m(x))$ is a distance measure between $y_m$ and $F_m(x)$, and $S(x)$ is a stabilizing function, to obtain $\hat{x}$; and perform a multislice Computed Tomography (CT) reconstruction to obtain an image using the obtained $\hat{x}$, wherein a weight of $S(x)$ is adaptively adjusted at locations of discontinuities within the reconstructed image.

20. A computer readable medium encoded with a program configured to instruct a computer to:
   utilize a cost function including a stabilizing function $S(x)$ to obtain a $\hat{x}$ which achieves a minimum summation; and
   generating an image by performing multislice Computed Tomography CT reconstruction using the obtained $\hat{x}$, wherein a weight of $S(x)$ is adaptively adjusted at locations of discontinuities within the reconstructed image.

21. A method of reconstructing an image, said method comprising:
   substantially minimizing a cost function including a weight $b_{i,j}$, wherein $b_{i,j}$ is adaptively chosen based upon at least one measure of local smoothness, wherein i and j are indices that respectively distinguish voxels $x_i$ and $x_j$; and
   generating an image using results from the cost function, wherein the weight $b_{i,j}$ is adaptively adjusted at locations of discontinuities within the reconstructed image.

22. A method in accordance with claim 21 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m, F_m(x))$ is a distance measure between $y_m$ and $F_m(x)$, and $S(x)$ is a stabilizing function, to obtain $\hat{x}$, wherein $S(x)$ has the form of $$S(x) = \sum_{[i,j] \in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

23. A method of reconstructing an image, said method comprising:
   substantially minimizing a cost function including a weight $b_{i,j}$, wherein $b_{i,j}$ is spatially adaptive based upon differences of pixels in a reconstruction, wherein i and j are indices that respectively distinguish voxels $x_i$ and $x_j$; and
   generating an image using results from the cost function, wherein the weight $b_{i,j}$ is adaptively adjusted at location of discontinuities within the reconstructed image.

24. A method in accordance with claim 23 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m, F_m(x))$ is a distance measure between $y_m$ and $F_m(x)$, and $S(x)$ is a stabilizing function, to obtain $\hat{x}$, wherein $S(x)$ has the form of $$S(x) = \sum_{[i,j] \in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

25. A method of reconstructing an image, said method comprising:
   substantially minimizing a cost function including a weight $b_{i,j}$, wherein $b_{i,j}$ is determined in accordance with
   $b_{i,j} = b_{(2m,2n),(2k,2l)} = |L_{(m,n)} - L_{(k,l)}|$, where $L_{(m,n)}$ is a pixel in the reconstruction with less resolution, $L_{(k,l)}$ is a pixel in the reconstruction with greater resolution, and $2 \geq p \geq 1$,
   wherein i and j are indices that respectively distinguish voxels $X_i$ and $X_j$, m and n are the respective row and the column indices of $L_{(m,n)}$ and k and l are the respective row and the column indices of $L_{(k,l)}$, and wherein p is an exponential function; and generating an image using results from the cost function, wherein the weight $b_{i,j}$ is adaptively adjusted at locations of discontinuities within the reconstructed image.

26. A method in accordance with claim 25 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where M is a factor of summation, $\hat{x}$ is the value of x which achieves the minimum summation, $y_m$ is an integral projection, $F_m(x)$ is a forward projection function, $D_m(y_m,F_m(x))$ is a distance measure between $y_m$ and $F_m(x)$, and $S(x)$ is a stabilizing function, to obtain $\hat{x}$, wherein $S(x)$ has the form of $$S(x) = \sum_{\{i,j\}\in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

27. A method of reconstructing an image, said method comprising:
  reconstructing a first image;
  segmenting the first image; and
  adaptively determining a weight $b_{i,j}$ based upon the segmentation;
  substantially minimizing a cost function including the weight $b_{i,j}$, wherein i and j are indices that respectively distinguish voxels $X_i$ and $X_j$; and
  generating an image using results from the cost function, wherein the weight $b_{i,j}$ is adaptively adjusted at locations of discontinuities within the reconstructed image.

28. A method in accordance with claim 27 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m,F_m(x))$ is a distance measure between $y_m$ and $F_m(x)$, and $S(x)$ is a stabilizing function, to obtain $\hat{x}$, wherein $S(x)$ has the form of $$S(x) = \sum_{\{i,j\}\in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

29. A method of reconstructing an image, said method comprising:
  substantially minimizing a cost function including a weight $b_{i,j}$, wherein $b_{i,j}$ is adaptively chosen based upon at least one local property of a material, wherein i and j are indices that respectively distinguish voxels $x_i$ and $x_j$; and
  generating an image using results from the cost function, wherein the weight $b_{i,j}$ is adaptively adjusted at locations of discontinuities within the reconstructed image.

30. A method in accordance with claim 29 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m,F_m(x))$ is a distance measure between $y_m$ and $F_m(x)$, and $S(x)$ is a stabilizing function, to obtain $\hat{x}$, wherein $S(x)$ has the form of $$S(x) = \sum_{\{i,j\}\in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

31. A method of reconstructing an image, said method comprising:
  receiving a clinical protocol;
  adaptively determining a weight $b_{i,j}$ based on the received protocol, wherein i and j are indices that respectively distinguish voxels $x_i$ and $x_j$;
  substantially minimizing a cost function including the weight $b_{i,j}$; and
  generating an image using results from the cost function, wherein the weight $b_{i,j}$ is adaptively adjusted at locations of discontinuities within the reconstructed image.

32. A method in accordance with claim 31 wherein said substantially minimizing comprises substantially minimizing a cost function of the form $$\hat{x} = \underset{x}{\operatorname{argmin}}\left\{\sum_{m=0}^{M} D_m(y_m, F_m(x)) + S(x)\right\},$$

where $\hat{x}$ is the value of x which achieves the minimum summation, $y_m$ is an integral projection, $F_m(x)$ is a forward projection function, $D_m(y_m,F_m(x))$ is a distance measure between $y_m$ and $F_m(x)$, and $S(x)$ is a stabilizing function, to obtain $\hat{x}$, wherein $S(x)$ has the form of $$S(x) = \sum_{\{i,j\}\in N} \rho\left(\frac{x_i - x_j}{\sigma b_{i,j}}\right),$$

where $\rho$ is a function, and $\sigma$ is a weight, and said using results comprises using the obtained $\hat{x}$ to generate an image.

\* \* \* \* \*